(12) United States Patent
Karimi et al.

(10) Patent No.: US 8,226,927 B2
(45) Date of Patent: Jul. 24, 2012

(54) $^{11}$C/$^{18}$F-LABELED INHIBITORS OF GLYCOGEN SYNTHASE KINASE-3

(76) Inventors: Farhad Karimi, Mansfield, MA (US); Bengt Langstrom, Uppsala (SE)

( * ) Notice: Subject to any disclaimer, the term of this patent is extended or adjusted under 35 U.S.C. 154(b) by 553 days.

(21) Appl. No.: 12/301,648

(22) PCT Filed: May 21, 2007

(86) PCT No.: PCT/IB2007/001308
§ 371 (c)(1), (2), (4) Date: Nov. 20, 2008

(87) PCT Pub. No.: WO2007/138408
PCT Pub. Date: Dec. 6, 2007

(65) Prior Publication Data
US 2009/0285756 A1    Nov. 19, 2009

Related U.S. Application Data

(60) Provisional application No. 60/808,480, filed on May 25, 2006.

(51) Int. Cl.
*A61K 51/00* (2006.01)

(52) U.S. Cl. ............... 424/1.65; 424/1.11; 424/1.89; 424/1.81; 424/1.85; 424/9.1

(58) Field of Classification Search .................. 424/1.65
See application file for complete search history.

(56) References Cited

U.S. PATENT DOCUMENTS

| 7,553,942 B2 * | 6/2009 | Itsenko et al. | ................ 534/11 |
| 2004/0006095 A1 * | 1/2004 | Zhang et al. | ................ 514/256 |

FOREIGN PATENT DOCUMENTS

| WO | 01/81345 | 11/2001 |
| WO | 2005/061516 | 7/2005 |
| WO | 2006/003414 | 1/2006 |

OTHER PUBLICATIONS

Iwata et al. Applied Radiation and Isotopes, 2002, 347-352.*
PCT/IB2007/001308 Int'l Search Report/Written Opinion dated Oct. 2007.

* cited by examiner

*Primary Examiner* — Michael G Hartley
*Assistant Examiner* — Sean R Donohue

(57) ABSTRACT

The present invention relates to new $^{11}$C/$^{18}$F-labeled inhibitor compounds for over-expressed GSK-3 prepared from the GMP synthesis method. The present invention provides novel $^{11}$C/$^{18}$F inhibitor compounds for over-expressed GSK-3 that are suitable for use as an in vivo imaging agent. A pharmaceutical comprising the compound and a kit for the preparation of the pharmaceutical are also provided.

4 Claims, No Drawings

[11]C/$^{18}$F-LABELED INHIBITORS OF GLYCOGEN SYNTHASE KINASE-3

This application is a filing under 35 U.S.C. 371 of international application number PCT/IB2007/001308, filed May 21, 2006, which claims priority to application No. 60/808,480 filed May 25, 2006, in The United States the entire disclosure of which is hereby incorporated by reference.

FIELD OF THE INVENTION

The present invention relates to new $^{11}$C/$^{18}$F-labeled inhibitor compounds for over-expressed GSK-3. The present invention provides novel $^{11}$C/$^{18}$F inhibitor compounds for over-expressed GSK-3 that are suitable for use as an in vivo imaging agent. A pharmaceutical comprising the compound and a kit for the preparation of the pharmaceutical are also provided.

BACKGROUND OF THE INVENTION

The progressive aging of the world's population brings on the undesired consequence of increasing the occurrence of senile dementia. Alzheimer's Disease ("AD") is a form of senile dementia. AD is a heterogeneous group of dementias that share common clinical symptoms, involving progressive cognitive impairments. This form of senile dementia is characterized by two kinds of pathological deposits in specific areas of the brain, called senile plaques and neurofibrillary tangles ("NFTs").

Senile plaques contain extracellular deposits of beta-amyloid protein ("Aβ") associated with degenerating nerve processes known as dystrophic neuritis. Initial deposits are non-fibrillar (a diffuse plaque), but are progressively transformed into fibrils, giving rise to the characteristic amyloid plaques. NFTs form inside neuronal cells that die during the course of the disease and consist primarily of adnormal paired helical filaments ("PHFs"). However, large numbers of senile plaques are found in some cognitively normal individuals, suggesting that not only their presence, but also the coexistence of NFTs is required for dementia. On the other hand, large numbers of NFTs in cerebral cortex and hippocampus closely correlate with the degree of dementia in AD. Thus, the accumulation of neurofibrillary lesions may represent a final pathway that leads to neuronal cell death and neuorodegeneration. *Dorronsoro et al.,* 2002, vol. 12, 1527-1536.

Furthermore, at the moment, researchers are trying to design new drugs useful in treatment of senile plaques and NFTs that are formed by PHFs whose main component is tau. PHF consists of hyperphosphorylated tau and contains a small amount of ubiquitin. Tau is one of the microtubule-associated proteins and is specifically localized in the neuron. The tau protein is essentially for stability of neuronal cytoskeleton, but in PBF, it is abnormally phosphorylated. Dorronsoro et al., 2002, vol. 12, 1527-1536.

Glycogen synthase kinase 3 beta ("GSK-3β") is involved in tau modifications leading to PHF. It is important to note that the inhibition of GSK-3β is accepted as a promising strategy for the treatment of AD and other neurodegenerative diseases.

GSK-3 is a key regulator of glycogen synthase, one of the principal modulators of glycogen metabolism and hence glucose levels. GSK-3 is a serine/threonine kinase for which two isoforms, GSK-3α and GSK-3β have been identified. These two isoforms share 97% sequence similarity within their kinase catalytic domains but differ significantly from one another outside this region, with GSK-3α possessing an extended N-terminal glycine-rich tail. The two isoforms are encoded by two different mRNAs that are variably expressed in different tissues. Accordingly, the GSK-3 β is highly expressed in the lungs, kidneys, and brain whereas the GSK-3α is highly expressed in the lungs, ovaries, kidneys, and testis. Furthermore, over expression of GSK-3β in the brain of adult mice was found to produce neurodegeneration exhibiting many of the characteristics of AD, including tau hyperphosphorylation. Indeed, an over-expressed GSK-3 has been linked to all the primary abnormalities associated with AD. The term over-expressed herein means to over manifest the effects of GSK-3. *Imahori et al.,* vol. 121, 179-188.

The number of GSK-3 inhibitors as therapeutic candidates in development is still limited. Which, in turn, leads us to the present invention. The present invention presents $^{11}$C and $^{18}$F labeled inhibitors of GSK-3 wherein these labeled inhibitors can be investigated by a medical imaging technique such as Positron Emission Tomography ("PET"), MRI, CT, ultrasound, X-ray imaging, or optical imaging.

Before moving forward, it is important to further characterize the relationship between PET and $^{11}$C and [18]F. A group of diagnostic Positron Emission Tomography ("PET") procedures utilize radioactive labeled compounds, wherein the radioactive atoms are positron emitters. Some examples of positron emitting elements include nuclides of carbon, nitrogen, or fluorine. These elements are the backbone of almost all biological active compounds. In order to be able to use these elements, stable isotopes are replaced with a radioactive isotope. The radioactive labeled compounds, called tracers, are transported, accumulated and converted exactly the same way as for non-radioactive compounds. The PET method has possibilities to detect malfunction on a cellular level in the investigated tissues or organs. The method is very sensitive and requires only nanomole quantities of produced radioactive tracers. These radioactive tracers have a half-life in the range from 2 to 110 minutes, (e.g. [11]C, $t_{1/2}$=20.4 minutes, $^{18}$F, $t_{1/2}$=110 minutes). *Acta Upsaliensis,* Uppsala 2002, ISBN 91-554-5452-6. Because of the radioactivity, the short half-lives and the submicromolar amounts of the labeled substances, extraordinary synthetic procedures are required for the production of these tracers.

Some peptides such as a heat resistant GSK-3 binding protein and a synthetic peptide inhibitor have recently been reported as GSK-3 inhibitors. Other reported GSK-3 inhibitors include purine and pyrimidine derivative compounds, azoles, maleimide derivatives, and ATP-non-competitive inhibitors are in development or have been discovered. However, radiolabeled inhibitors have not been reported. Accordingly, the present invention introduces novel $^{11}$C/$^{18}$F-labeled analogue inhibitors of GSK-3 that can then be investigated by medical imaging techniques.

Discussion or citation of a reference herein shall not be construed as an admission that such reference is prior art to the present invention.

SUMMARY OF THE INVENTION

In view of the needs of the prior art, the present invention provides novel $^{11}$C/$^{18}$F-labeled inhibitor compounds for over-expressed GSK-3. The present invention also provides novel $^{11}$C/$^{18}$F inhibitor compounds for over-expressed GSK-3 that are suitable for use as an in vivo imaging agent. A pharmaceutical comprising the compound and a kit for the preparation of the pharmaceutical are also provided.

The [$^{11}$C/$^{18}$F]-labeled inhibitor compounds of the present invention are obtained through Good Manufacturing Practice ("GMP") syntheses. GMP is part of Quality Assurance which ensures that products are consistently produced and controlled to the quality standards appropriate to their intended use and as required by the Marketing Authorization.

One embodiment of the present invention encompasses a compound of formula (I),

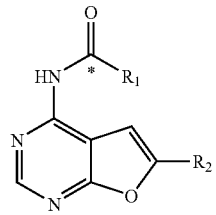

(I)

or a salt or solvate thereof, wherein said compound is labeled with an imaging moiety, and wherein $R_1$=an alkyl or an aryl, and $R_2$=alkyl or an aryl and its derivatives.

Another embodiment encompasses a compound of formula (II),

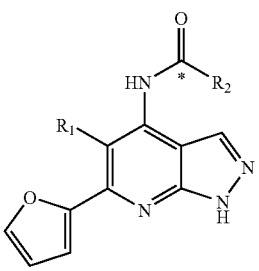

(II)

or a salt or solvate thereof, wherein said compound is labeled with an imaging moiety, and wherein, $R_1$=F, Cl, Br, I, or an alkyl (n=1-5), alkoxide (n=1-5) and $R_2$=alkyl or an aryl and its derivatives.

A further embodiment of the present invention depicts a compound of formula (III) and (IIIa),

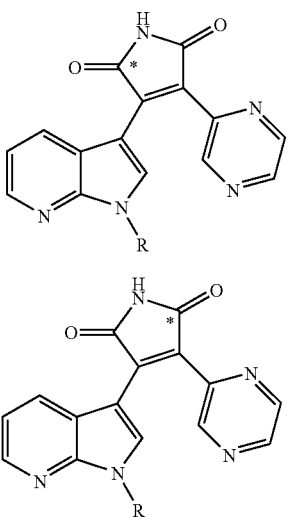

(III)

(IIIa)

or a salt or solvate thereof, wherein said compounds are labeled with an imaging moiety, and wherein R=$(CH_2)_n{}^{18}F$ or a similar structure.

Yet, another embodiment shows a kit comprising the formula of compound (I),

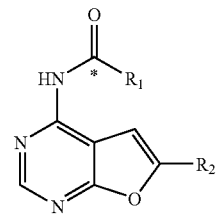

(I)

or a salt or solvate thereof, wherein said compound is labeled with an imaging moiety, and wherein, $R_1$=an alkyl or an aryl, $R_2$=alkyl or an aryl and its derivatives further wherein said kit is suitable for the preparation of a pharmaceutical composition which comprises compound (I), wherein the imaging moiety is a radioactive moiety, together with a biocompatible carrier in a form suitable for mammalian administration.

A further embodiment depicts a kit comprising the formula of compound (II),

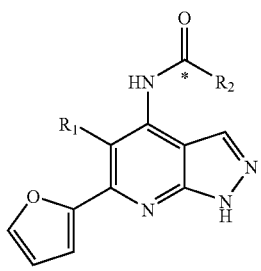

(II)

or a salt or solvate thereof, wherein said compound is labeled with an imaging moiety, and wherein, $R_1$=F, Cl, Br, I, or an alkyl (n=1-5), alkoxide (n=1-5) and $R_2$=alkyl or an aryl and its derivatives further wherein said kit is suitable for the preparation of a pharmaceutical composition which comprises compound (II), wherein the imaging moiety is a radioactive moiety, together with a biocompatible carrier in a form suitable for mammalian administration.

The present invention also shows a kit comprising the formula of compound (III) and (IIIa),

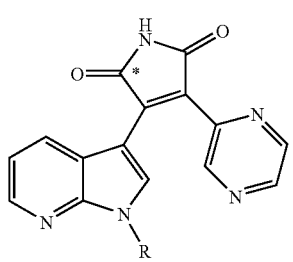

(III)

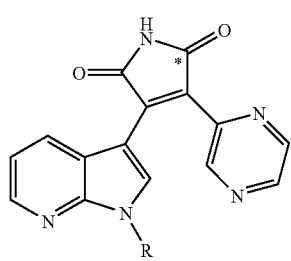

(IIIa)

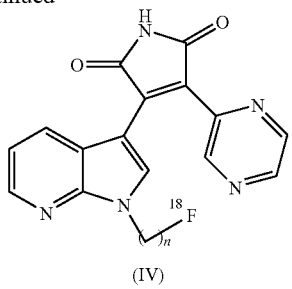

(IV)

or a salt or solvate thereof, wherein said compounds are labeled with an imaging moiety, and wherein R=(CH$_2$)$_n$$^{18}$F or a similar structure, further wherein said kit is suitable for the preparation of a pharmaceutical composition which comprises compound (III), wherein the imaging moiety is a radioactive moiety, together with a biocompatible carrier in a form suitable for mammalian administration.

Yet another embodiment entails a compound of formula (IV),

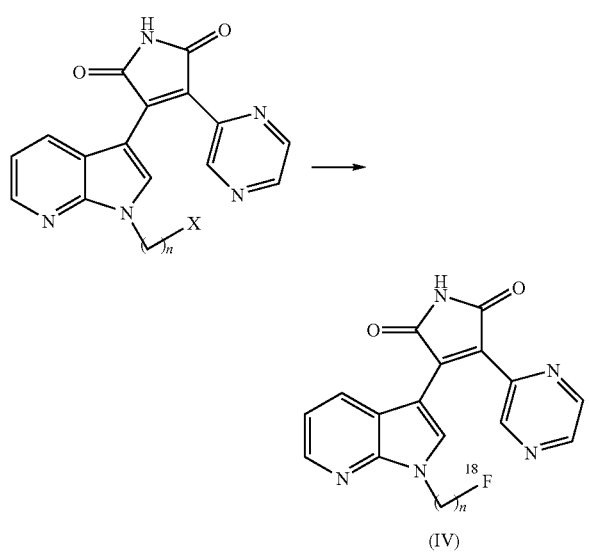

(IV)

or a salt or solvate thereof, wherein said compound is labeled with an imaging moiety, and wherein X=Cl, Br, I, OTs, OMs, or any ponytail sulfonate.

Still another embodiment entails a kit comprising the formula of compound (IV),

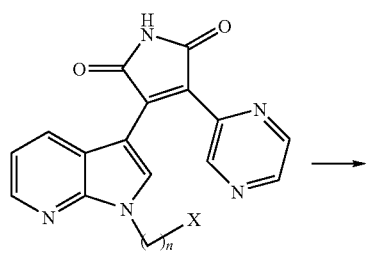

or a salt or solvate thereof, wherein said compound is labeled with an imaging moiety, and wherein, R$_1$=an alkyl or an aryl, R$_2$=alkyl or an aryl and its derivatives further wherein said kit is suitable for the preparation of a pharmaceutical composition which comprises compound (IV), wherein the imaging moiety is a radioactive moiety, together with a biocompatible carrier in a form suitable for mammalian administration.

DETAILED DESCRIPTION OF THE INVENTION

Glycogen synthase kinase-3 ("GSK-3") has recently emerged in the field of medicinal chemistry as one of the most attractive therapeutic targets for the development of selective inhibitors as promising new drugs for numerous serious pathologies, including Alzheimer's disease ("AD"), stroke, bipolar disorders, chronic inflammatory processes, cancer and Type II diabetes.

GSK-3 is an enzyme with a diverse range of actions in intercellar signaling pathways. It plays a crucial role in several human diseases and therefore has great potential for therapeutic intervention. Knowledge of the role of GSK-3 inhibitors in many different cellular processes has increased over the last five years.

A number of diverse drug-like molecules (small molecules capable of crossing biological barriers such as the blood-brain barrier and gastrointestinal tract) have emerged. However, agents for clinical use must be able to specifically target the appropriate enzymatic process. Nonspecific protein kinase inhibition by ATP site-directed inhibitors might have widespread undesirable effects. This is the case in the majority of GSK-3 inhibitors discovered to date. All show activity on many other kinases, thus diminishing their drug development possibilities. It is important to note here that ATP is an adenosine-derived nucleotide, $C_{10}H_{16}N_5O_{13}P_3$, that contains high-energy phosphate bonds and is used to transport energy to cells for biochemical processes, including muscle contraction and enzymatic metabolism.

After obtaining the $^{11}$C/$^{18}$F-labeled inhibitor compounds, using an automated system termed FastLab or Tracerlab, high performance liquid chromatography ("HPLC") is used to verify the structure of the analogues. A further tool was used to verify the structure of the analogues wherein a calculation study was conducted to look into the physical properties and 3D images of various analogues. The calculation study was conducted using a computer-aided molecular design modeling tool also know as CAChe. CAChe enables one to draw and model molecules as well as perform calculations on a molecule to discover molecular properties and energy values. The calculations are performed by computational applications, which apply equations from classical mechanics and quantum mechanics to a molecule. For example, the claimed novel compounds of formulas (I), (II), (III). and (IIIa) were designed using CAChe.

An embodiment of the present invention depicts a compound of formula (I),

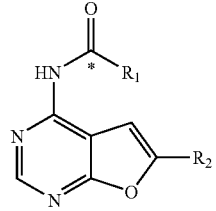

or a salt or solvate thereof, wherein said compound is labeled with an imaging moiety, and wherein $R_1$=an alkyl or an aryl, and $R_2$=alkyl or an aryl and its derivatives.

Yet another embodiment shows a compound of formula (II),

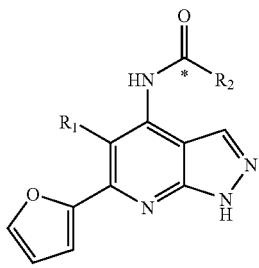

or a salt or solvate thereof, wherein said compound is labeled with an imaging moiety, and wherein, $R_1$=F, Cl, Br, I, or an alkyl (n=1-5), alkoxide (n=1-5) and $R_2$=alkyl or an aryl and its derivatives.

A further embodiment of the present invention shows compounds of formulas (III) and (IIIa),

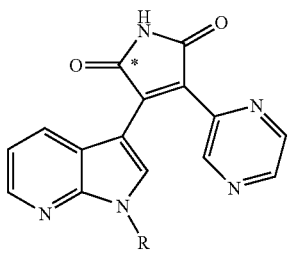

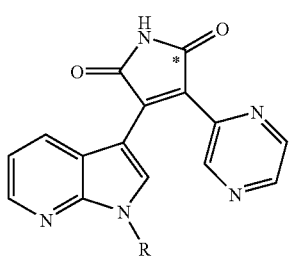

or a salt or solvate thereof, wherein said compounds are labeled with an imaging moiety, and wherein R=$(CH_2)_n{}^{18}F$ or a similar structure.

In one embodiment of the present invention of the compound of formula (I), the imaging moeity comprises a positron-emitting radioactive non-metal is disclosed.

Yet in another embodiment of the compound of formula (I), said imaging moeity is a positron-emitting radioactive non-metal selected from the group consisting of $^{11}C$ and $^{18}F$ is also disclosed.

A further embodiment of the compound of formula (II), is wherein said imaging moeity comprises a positron-emitting radioactive non-metal.

Another embodiment of the compound of formula (II) is wherein said imaging moiety is a positron-emitting radioactive non-metal selected from the group consisting of $^{11}C$ and $^{18}F$. Yet a further embodiment is wherein the compound wherein the formula (II) of said imaging moiety comprises a positron-emitting radioactive non-metal.

Still another embodiment of the present invention encompasses compounds of formula (III) and (IIIa), wherein said imaging moiety is a positron-emitting radioactive non-metal selected from the group consisting of $^{11}C$ and $^{18}F$.

An additional embodiment of the present invention comprises a pharmaceutical composition of the compound of formula (I), wherein the imaging moiety is a radioactive moiety, together with a biocompatible carrier in a form suitable for mammalian administration.

A further embodiment of the present invention comprises a pharmaceutical composition according to the compound of formula (I), wherein the pharmaceutical composition is a radiopharmaceutical.

Yet another embodiment comprises a pharmaceutical composition which comprises the compound of formula (II), wherein the imaging moiety is a radioactive moiety, together with a biocompatible carrier in a form suitable for mammalian administration.

A further embodiment encompasses the pharmaceutical composition according to the compound of formula (II), wherein the pharmaceutical composition is a radiopharmaceutical.

Another embodiment comprises a pharmaceutical composition of the compound of formula (III) and (IIIa), wherein the imaging moiety is a radioactive moiety, together with a biocompatible carrier in a form suitable for mammalian administration.

Still another embodiment entails the pharmaceutical composition according to the compounds of formulas (III) and (IIIa), wherein the pharmaceutical composition is a radiopharmaceutical.

Yet another embodiment encompasses a kit comprising the formula of compound (I),

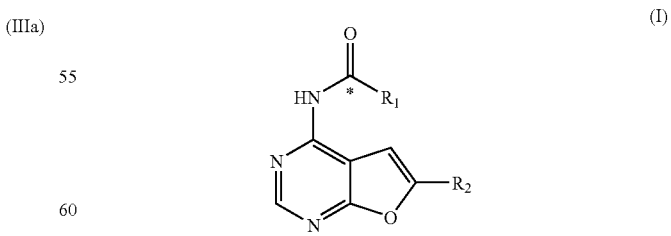

or a salt or solvate thereof, wherein said compound is labeled with an imaging moiety, and wherein, $R_1$=an alkyl or an aryl, $R_2$=alkyl or an aryl and its derivatives further wherein said kit is suitable for the preparation of a pharmaceutical composition which comprises compound (I), wherein the imaging moiety is a radioactive moiety, together with a biocompatible carrier in a form suitable for mammalian administration.

Yet a further embodiment encompasses a method for the in vivo diagnosis or imaging of an over-expressed GSK-3 in a subject, comprising administration of a pharmaceutical composition comprising a compound of formula (I).

Still a further embodiment encompasses a method of monitoring the effect of treatment of a human or animal body with a drug to combat an over-expressed GSK-3, wherein said method comprising administering to said body the pharmaceutical composition of the compound of formula (I), and detecting the uptake of said pharmaceutical.

Another embodiment encompasses a kit comprising the formula of compound (II),

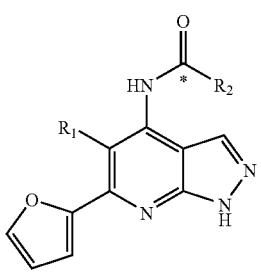

(II)

or a salt or solvate thereof, wherein said compound is labeled with an imaging moiety, and wherein, $R_1$=F, Cl, Br, I, or an alkyl (n=1-5), alkoxide (n=1-5) and $R_2$=alkyl or an aryl and its derivatives further wherein said kit is suitable for the preparation of a pharmaceutical composition which comprises compound (II), wherein the imaging moiety is a radioactive moiety, together with a biocompatible carrier in a form suitable for mammalian administration.

Still a further embodiment entails a method for the in vivo diagnosis or imaging of an over-expressed GSK-3 in a subject, comprising administration of a pharmaceutical composition comprising a compound of the formula (II).

Another embodiment encompasses a method of monitoring the effect of treatment of a human or animal body with a drug to combat an over-expressed GSK-3, wherein said method comprising administering to said body the pharmaceutical composition of the compound of formula (II), and detecting the uptake of said pharmaceutical.

Still another embodiment entails a kit comprising the formulas of compounds (III) and (IIIa),

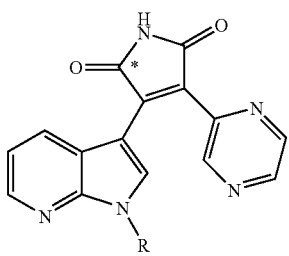

(III)

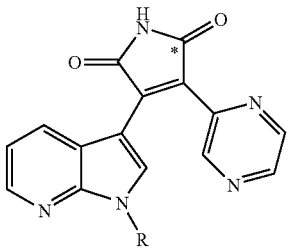

(IIIa)

or a salt or solvate thereof, wherein said compounds are labeled with an imaging moiety, and wherein R=$(CH_2)_n{}^{18}F$ or a similar structure, further wherein said kit is suitable for the preparation of a pharmaceutical composition which comprises compounds (III) and (IIIa), wherein the imaging moiety is a radioactive moiety, together with a biocompatible carrier in a form suitable for mammalian administration.

Yet another embodiment comprises a method for the in vivo diagnosis or imaging of an over-expressed GSK-3 in a subject, comprising administration of a pharmaceutical composition comprising a compound of formulas (III) and (IIIa).

Still a further embodiment encompasses a method of monitoring the effect of treatment of a human or animal body with a drug to combat an over-expressed GSK-3, wherein said method comprising administering to said body the pharmaceutical composition of the compounds of formulas (III) and (IIIa), and detecting the uptake of said pharmaceutical.

Yet another embodiment entails a compound of formula (IV),

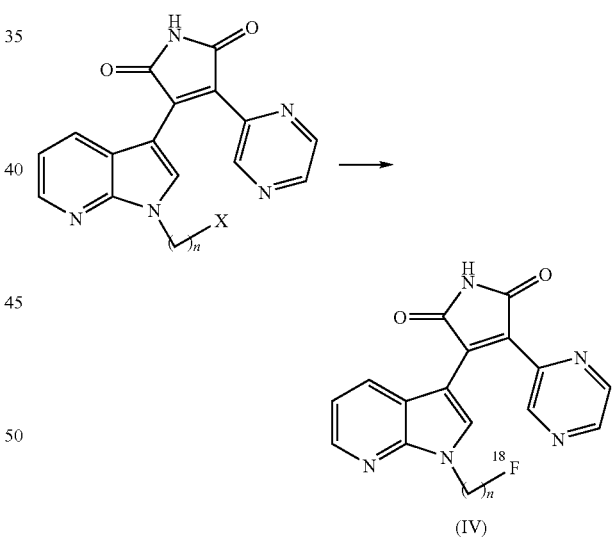

(IV)

or a salt or solvate thereof, wherein said compound is labeled with an imaging moiety, and wherein X=Cl, Br, I, OTs, OMs, or any ponytail sulfonate.

A further embodiment encompasses the compound of formula (IV), wherein said imaging moeity comprises a positron-emitting radioactive non-metal. Another embodiment of the compound of formula (IV) is wherein said imaging moeity is a positron-emitting radioactive non-metal selected from the group consisting of $^{11}C$ and $^{18}F$.

Also an embodiment of the present invention entails a pharmaceutical composition which comprises the compound of formula (IV), wherein the imaging moiety is a radioactive moiety, together with a biocompatible carrier in a form suitable for mammalian administration.

A further embodiment encompasses the pharmaceutical composition according to the compound of formula (IV), wherein the pharmaceutical composition is a radiopharmaceutical.

Still another embodiment entails a kit comprising the formula of compound (IV),

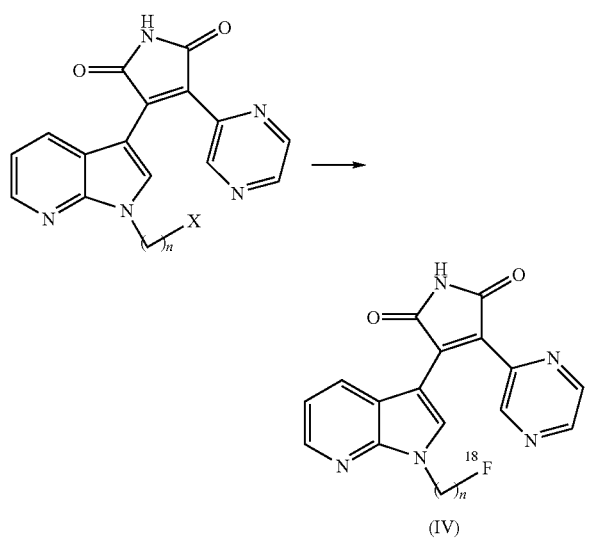

(IV)

or a salt or solvate thereof, wherein said compound is labeled with an imaging moiety, and wherein, $R_1$=an alkyl or an aryl, $R_2$=alkyl or an aryl and its derivatives further wherein said kit is suitable for the preparation of a pharmaceutical composition which comprises compound (IV), wherein the imaging moiety is a radioactive moiety, together with a biocompatible carrier in a form suitable for mammalian administration.

A further embodiment entails a method for the in vivo diagnosis or imaging of an over-expressed GSK-3 in a subject, comprising administration of a pharmaceutical composition comprising a compound of formula (IV).

Yet another embodiment encompasses a method of monitoring the effect of treatment of a human or animal body with a drug to combat an over-expressed GSK-3, said method comprising administering to said body the pharmaceutical composition of a compound of formula (IV), and detecting the uptake of said pharmaceutical The "imaging moiety" used herein is a radioactive moiety such as $^{11}C$ and $^{18}F$ or a positron-emitting radioactive non-metal.

The "biocompatible carrier" described herein is a fluid, especially a liquid, in which the compound is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

Furthermore, the pharmaceutical compositions are suitably supplied in either a container which is provided with a seal which is suitable for single or multiple puncturing with a hypodermic needle (e.g. a crimped-on septum seal closure) whilst maintaining sterile integrity. Such containers may contain single or multiple patient doses. Preferred multiple dose containers comprise a single bulk vial (e.g. of 10 to 30 cm$^3$ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and are therefore preferably a disposable or other syringe suitable for clinical use. For radiopharmaceutical compositions, the pre-filled syringe may optionally be provided with a syringe shield to protect the operator from radioactive dose. Suitable such radiopharmaceutical syringe shields are known in the art and preferably comprise either lead or tungsten. The radiopharmaceuticals may be administered to patients for SPECT or PET imaging in amounts sufficient to yield the desired signal, typical radionuclide dosages of 0.01 to 100 mCi, preferably 0.1 to 50 mCi will normally be sufficient per 70 kg bodyweight.

Suitable kit containers comprise a sealed container which permits maintenance of sterile integrity and/or radioactive safety, plus optionally an inert headspace gas (e.g. nitrogen or argon), whilst permitting addition and withdrawal of solutions by syringe. A preferred such container is a septum-sealed vial, wherein the gas-tight closure is crimped on with an overseal (typically of aluminium). Such containers have the additional advantage that the closure can withstand vacuum if desired e.g. to change the headspace gas or degas solutions.

An in vivo diagnostic or imaging method, e.g. SPECT or PET relates to the in vivo imaging of GSK-3 inhibitor compounds and therefore has utility in the diagnosis of over expressed GSK-3-related conditions. Examples of over expressed GSK-3 inhibitor compounds include AD, and other neurodegenerative diseases.

Example 1

Experimental Studies

General Method for Preparing Novel
$^{11}C/^{18}F$-Labeled Inhibitor Compounds of Glycogen
Synthase Kinase-3

Synthesis of Novel Compounds I and II:
A capped vial (1 mL) containing a solution of tetrakis(triphenylphosphine)-palladium(0) and corresponding aryl iodide in dry THF was flushed with nitrogen gas. Amine was added and the reaction mixture was shaken just before injection into the micro-autoclave pre-charged with $^{11}CO$. The micro-autoclave was heated at 100-150° C. for 5 minutes. The crude product was placed in a pre-evacuated vial (3 mL).
Synthesis of Novel Compounds III and IIIa:
The synthesis of the compounds of formulas (III) and (IIIa) of the present invention are depicted as follows:

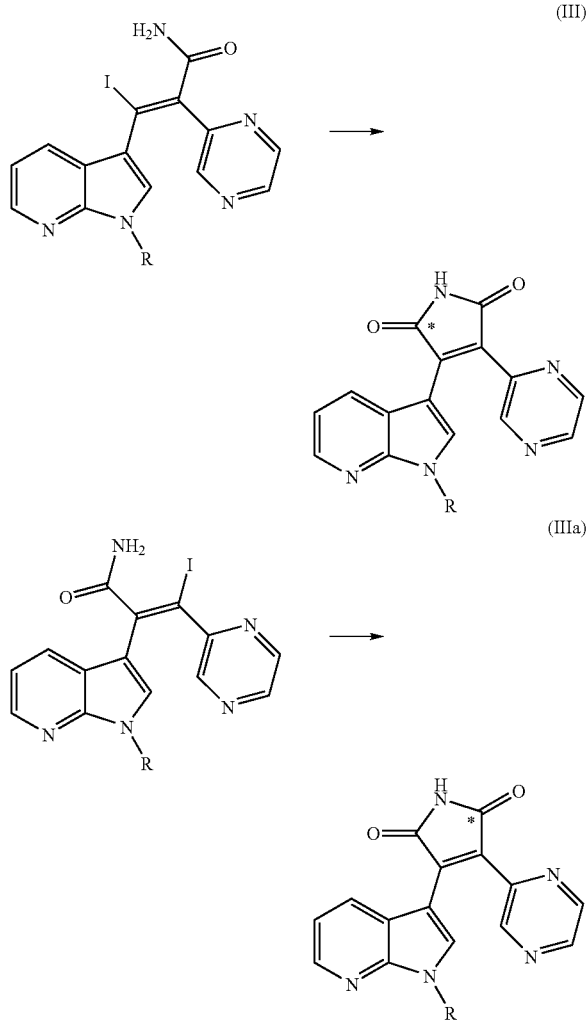

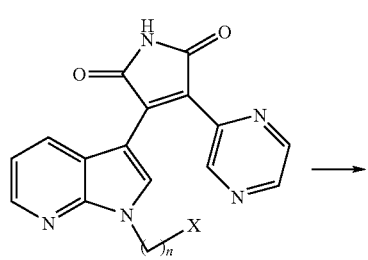

A capped vial (1 mL) containing a solution of tetrakis(triphenylphosphine)-palladium(0) and corresponding precursor in dry THF was flushed with nitrogen gas. The reaction mixture was heated at 100-150° C. for 5 minutes. The crude product was placed in a pre-evacuated vial (3 mL).

FIG. 1 also depicts the general synthesis of compounds of formulas (III) and (IIIa) in order to form novel $^{11}$C. and $^{18}$F-labeled inhibitor compounds of glycogen synthase kinase-3.

Synthesis of Novel $^{11}$C and $^{18}$F-Labeled Inhibitor Compounds of Glycogen Synthase-Kinase-3

The general synthesis of compounds of formulas (III) and (IIIa) in order to form novel $^{11}$C and $^{18}$F-labeled inhibitor compounds of glycogen synthase kinase-3 is as follows:

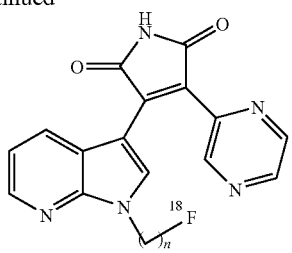

wherein X=Cl, Br, I, OTs, OMs, or any ponytail sulfonate.

$^{18}$F Production

[$^{18}$F] Fluoride was produced at Uppsala Imanet by the $^{18}$O (p, n) $^{18}$F nuclear reaction through proton irradiation of enriched (95%) 18O water using Scanditronix MC-17 cyclotron.

Preparation of the [K/2.2.2]$^{+18}$F$^-$ (Using Enriched 95% $^{18}$O Water)

After irradiation, the target content was passed through a column packed with QMA resin. The column was purged with helium for 5 min. The [$^{18}$F]fluoride adsorbed on the resin was eluted into a reaction vial with 4 ml of a 96:4 (by volume) acetonitrile-water mixture containing 19.1 mg of kryptofix 2.2.2 and 2.9 mg of K$_2$CO$_3$; the solution was then evaporated and co-evaporated with anhydrous acetonitrile (2×1 ml) to dryness in a nitrogen stream at 110° C. After drying procedure the vial was cooled to 40-50° C. during 3-4 min.

$^{18}$F-Labeling

A solution of corresponding precursor (4-5 mg) in 0.2 ml of acetonitrile or dry DMF was added to a dry residue containing the complex [K/K2.2.2]$^{+18}$F$^-$ in 0.2 ml of acetonitrile or dry DMF. The reaction was performed in a closed vessel at 150° C. for 15 min.

Specific Embodiments, Citation of References

The present invention is not to be limited in scope by specific embodiments described herein. Indeed, various modifications of the inventions in addition to those described herein will become apparent to those skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A compound of formula (IV):

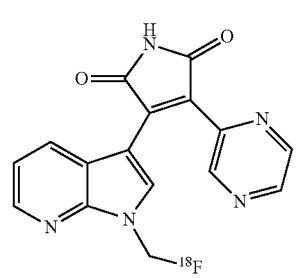

or a salt or solvate thereof.

2. A pharmaceutical composition which comprises the compound of claim 1, together with a biocompatible carrier in a form suitable for mammalian administration.

3. The pharmaceutical composition according to claim 2, wherein the pharmaceutical composition is a radiopharmaceutical.

4. A kit suitable for the preparation of a pharmaceutical composition comprising a compound according to claim 1.

* * * * *